United States Patent [19]

Saito et al.

[11] 3,988,359
[45] Oct. 26, 1976

[54] CATALYST FOR USE IN AND PROCESS FOR PREPARING ACRYLONITRILE

[75] Inventors: Shigeru Saito, Fuchu; Yutaka Sasaki, Yokohama; Tomio Nakamura, Ichikawa; Kiyoshi Moriya, Kanagawa; Yoshimi Nakamura, Kawasaki; Hiroshi Utsumi, Yokohama, all of Japan

[73] Assignee: Nitto Chemical Industry Co., Ltd., Tokyo, Japan

[22] Filed: Feb. 10, 1975

[21] Appl. No.: 548,839

[30] Foreign Application Priority Data

Feb. 9, 1974   Japan.............................. 49-15885

[52] U.S. Cl............................. 260/465.3; 252/432; 252/437; 252/439
[51] Int. Cl.²................................... C07C 120/14
[58] Field of Search................................. 260/465.3

[56] References Cited
UNITED STATES PATENTS 3,668,147   6/1972   Yoshino et al.................. 252/435 X
3,716,496   2/1973   Yoshino et al................ 260/465.3 X

*Primary Examiner*—Joseph Paul Brust
*Attorney, Agent, or Firm*—Sughrue, Rothwell, Mion, Zinn & Macpeak

[57] ABSTRACT

A process for preparing acrylonitrile from propylene, which comprises contacting a mixture of propylene, molecular oxygen and ammonia in the vapor phase at a temperature of about 380° to about 500° C. and a pressure of about atmospheric pressure to about 3 Kg/cm²-G with a catalyst composition comprising active components of the following empirical formula $$Fe_aSb_bMe_cTe_dQ_eR_fO_g$$

wherein
Me is at least one element selected from the group consisting of V, Mo and W; Q is at least one element selected from the group consisting of Cu, Mg, Zn, La, Ce, Al, Cr, Mn, Co, Ni, Bi and Sn; and R is at least one element selected from the group consisting of P and B; $a$, $b$, $c$, $d$, $e$, $f$ and $g$ each represents atomic ratios, and when $a$ is 10, $15 \leq b \leq 60$, $1 < c \leq 10$, $0.5 \leq d \leq 10$, $0.1 \leq e \leq 10$, $0 \leq f \leq 5$, and $g$ represents the number of oxygen atoms corresponding to the oxides resulting from the combination of the above active components,
wherein the Me and Te components are substantially dissolved in an iron-antimony oxide compound (FeSbO₄) to form a solid solution when the composition is or has been, calcined finally at a temperature of about 500° C. to about 900° C.

10 Claims, 12 Drawing Figures

Fe/Sb (75/25 ATOMIC RATIO) 800°C CALCINATION

Fe/Sb (50/50 ATOMIC RATIO) 800°C CALCINATION

Fe/Sb (25/75 ATOMIC RATIO) 800°C CALCINATION

CATALYST 6

CATALYST 12

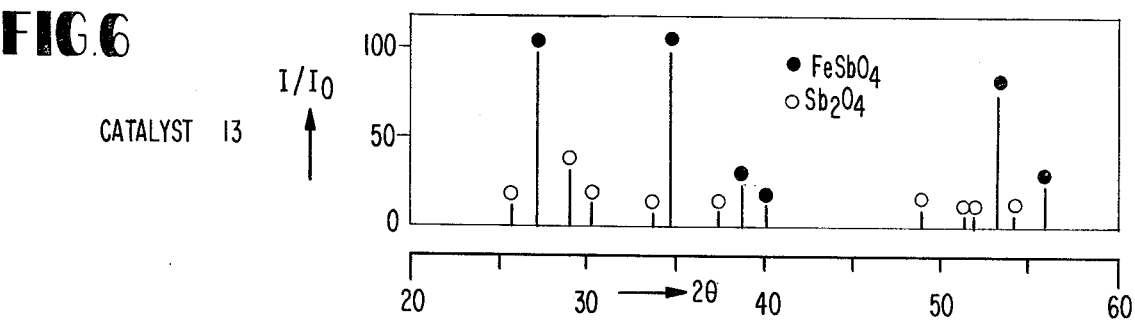
FIG.6 CATALYST 13
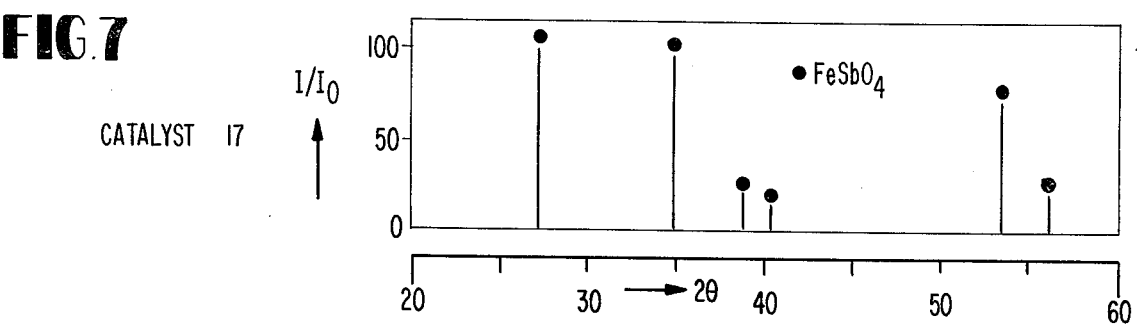
FIG.7 CATALYST 17
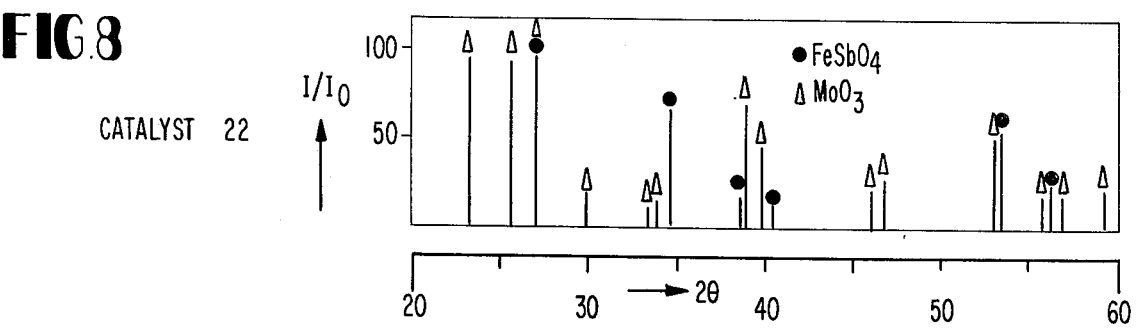
FIG.8 CATALYST 22
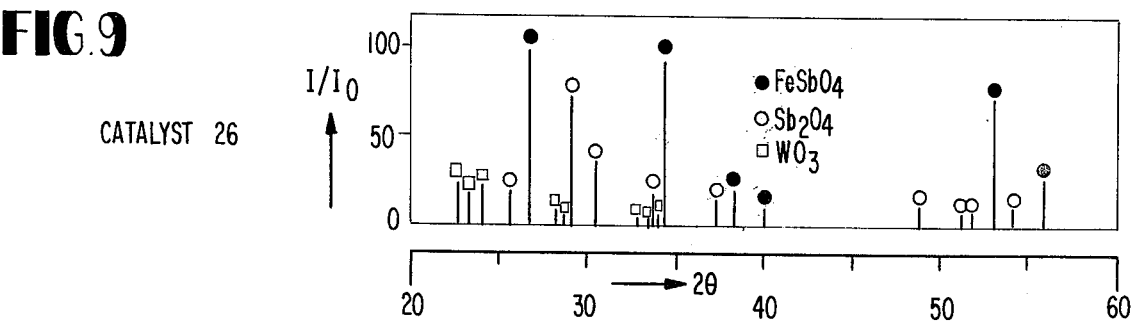
FIG.9 CATALYST 26

CATALYST FOR USE IN AND PROCESS FOR PREPARING ACRYLONITRILE

BACKGROUND OF THE INVENTION

1. Field of the Invention

This invention relates to a process for preparing acrylonitrile by the vapor-phase catalytic ammoxidation of propylene. More specifically, the invention relates to a process for preparing acrylonitrile by the vapor-phase catalytic ammoxidation of propylene using a multiple promoted iron oxide-antimony oxide catalyst having a specific catalytic structure.

2. Descriprion of the Prior Art

The output of acrylonitrile by the vapor-phase catalytic ammoxidation of propylene now amounts to a very large figure, and even a slight increase in the yield of acrylonitrile gives rise to a great economical advantage. Incessant efforts have therefore been made to develop catalysts of good performance for the production of acrylonitrile. In view of environmental problems, too, it has been strongly desired in recent years to provide catalysts which can be used to produce acrylonitrile in a higher yield and cause a reduction in the formation of by-products that are difficult to treat.

Well-known catalysts effective for the production of acrylonitrile by the vapor-phase catalytic ammoxidation of propylene are the catalyst composed mainly of bismuth phosphomolybdate described in U.S. Pat. No. 2,904,580 and the catalyst composed mmainly of an oxide of antimony and an oxide of uranium described in U.S. Pat. No. 3,198,750. These catalysts have been used commercially, but have not been found satisfactory with respect to the yield of acrylonitrile. Catalysts which bring about higher yields have also been proposed.

Further, an iron oxide-antimony oxide mixed catalyst is useful in the vapor-phase catalytic ammoxidation of propylene as disclosed in Japanese patent publication No. 19111/'63 (Japanese Pat. No. 420,264), U.S. Pat. No. 3,197,419 and British Pat. No. 983,755. Moreover, improved results are obtained by the addition of particular additives to such a catalyst as disclosed in U.S. Pat. Nos. 3,338,952, 3,542,843, 3,591,620, 3,668,147 and 3,716,496. These catalysts, however, have not proven to be entirely satisfactory with respect to the yield of acrylonitrile and in other properties.

With a view toward further improvements, the properties of the catalysts disclosed in U.S. Pat. Nos. 3,668,147 and 3,716,496 were discovered, and it was found that when these catalysts have a specific catalytic structure and contain a Me component (i.e., V, Mo and W) in an amount larger than that disclosed in these patents, further improvements in the production of acrylonitrile were exhibited.

SUMMARY OF THE INVENTION

Accordingly, it is an object of this invention to provide a process for preparing acrylonitrile by the vapor-phase catalytic ammoxidation of propylene, in which acrylonitrile can be obtained in a higher yield and which results in a high acrylonitrile yield over prolonged periods of time even if the ration of oxygen to propylene is low and also results in a high acrylonitrile yield even if the ratio of ammonia to propylene is low.

The above object of this invention is achieved using a multiple promoted iron oxide-antimony oxide catalyst having a specific catalyst structure and containing an oxide of iron, an oxide of antimony, an oxide of tellurium, an oxide of at least one metal selected from the group consisting of V, Mo and W and an oxide of at least one metal selected from the group consisting of Cu, Mg, Zn, La, Ce, Al, Cr, Mn, Co, Ni, Bi and Sn as essential components, and if desired further containing an oxide of P and/or B.

The process for preparing acrylonitrile by the vapor-phase catalytic ammoxidation of propylene in accordance with this invention comprises using a catalyst composition comprising active components of the empirical formula

$Fe_a Sb_b Me_c Te_d Q_e R_f O_g$ wherein Pi Me is at least one element selected from the group consisting of V, Mo and W; Q is at least one element selected from the group consisting of Cu, Mg, Zn, La, Ce, Al, Cr, Mn, Co, Ni, Bi and Sn, and R is at least one element selected from the group consisting of P and B; $a, b, c, d, e, f$ and $g$ each represents the atomic ratios, and when a is 10, $15 \leqq b \leqq 60$, $1 < c \leqq 10$, preferably $1.2 \leqq c \leqq 5$, $0.5 \leqq d \leqq 10$, $0.1 \leqq e \leqq 10$, $0 \leqq f \leqq 5$, and $g$ represents the number of oxygen atoms corresponding to the oxides resulting from the combination of the above components, i.e., g is 35.6 to 217.5, wherein the Me and Te components are substantially dissolved in an iron-antimony oxide compound (FeSbO₄) to form a solid solution when the composition is, or has been, calcined finally at a temperature of about 500° C. to about 900° C.

BRIEF DESCRIPTION OF THE DRAWINGS

FIGS. 4, 5, 6 and 7 show X-ray diffraction patterns of catalysts of the invention as produced in the examples.

FIGS. 8 and 9 show X-ray diffraction patterns of comparative catalysts used in the examples.

DETAILED DESCRIPTION OF THE INVENTION

Figure 1:
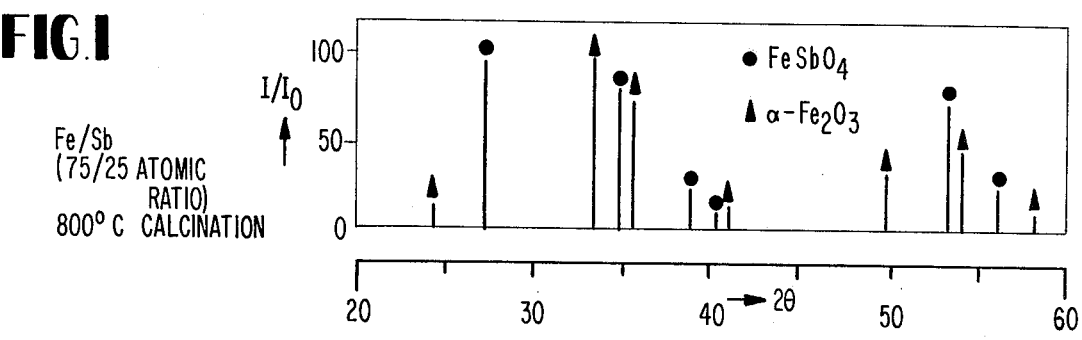
FIGS. 1, 2 and 3 show X-ray diffraction patterns of ironantimony oxide catalysts of varying atomic ratios.

U.S. Pat. No. 3,338,952 has attempted the addition of 25 metal elements to an iron-antimony catalyst and discloses the promoter effect of these metal elements. However, such a patent discloses only the promoter effect of metal elements added in an amount of 1 to 10 percent by weight into only one specific unpromoted iron oxide-antimony oxide catalyst having a very small atomic ratio of Fe/Sb (about 1/9 ). Also, the unpromoted catalyst has weak activity and the conversion of propylene to acrylonitrile obtained by using the catalyst is only 50%. Further, the changes in catalytic activities which would be caused by the quantitative variation of the promoter, by the combined use of the plural promoters and by the variation in the atomic ration of Fe/Sb in the unpromoted catalysts have not been taken into consideration.

U.S. Pat. No. 3,668,147 disclosed a catalyst represented by the empirical formula, $Fe_{10} Sb_{5-60} Me_{0.01-1} Te_{0.05-5} X_{0-1} O_{22-151}$ (wherein Me represents an element selected from the group consisting of V, Mo and W; and X represents an element selected from the group consisting of P and B), and the disclosure in this patent further is that, when the amount of the Me component added exceeds an atomic ratio to the Fe component of 1 to 10 of the Fe component, the absolute value of selectivity considerably falls, although there is an action of suppressing degradation at a low oxygen content.

In U.S. Pat. No. 3,716,496, a catalyst represented by the empirical formula, $Fe_{10} Sb_{20-60} Me_{0.01-1} Te_{0.05-5} Q_{0.1-20}$ (wherein Me represents an element selected from the group consisting of V, Mo and W; and Q represents an element selected from the group consisting of Cu, Ag, Be, Mg, Ca, Sr, Ba, Zn, Cd, La, Ce and Al). is disclosed. This U.S. Patent also discloses that the above-described Q component prevents the formation of "sticks" which are sometimes observed in the high temperature calcination step in a catalyst having a high Sb/Fe ratio.

However, it has now been found that, when all of the Me component and Te component as described above substantially forms a solid solution in an iron-antimony oxide compound ($FeSbO_4$), (1) the acrylonitrile selectivity is rather increased, not reduced; (2) the acrylonitrile selectivity is maintained over a long period of time even when the proportion of oxygen to propylene falls; and (3) the high acrylonitrile selectivity is maintained even when the proportion of ammonia to propylene falls, at ranges of, e.g., (a) an atomic ratio of the Me component being more than 1 but not greater than 10 per 10 of the Fe component, (b) an atomic ratio of the Te component being 0.5 to 10 per 10 of the Fe component, and (c) an atomic ratio of the Q component which is an element selected from the group consisting of Cu, Mg, Zn, La, Ce, Al, Cr, Mn, Co, Ni, Bi and Sn being 0.1 to 10 per 10 of the Fe component.

Furthermore, superficially, it might appear that there is only a slight difference between the catalyst of this invention and the catalysts of U.S. Pat. Nos. 3,668,147 and 3,716,496 in composition, but the catalyst of this invention surprisingly provides superior effects, which could not have been expected.

Whether the iron-antimony oxide acts effectively as a catalyst for ammoxidation of propylene and also as a catalyst for the oxidation and oxidative dehydrogenation of olefins is not only determined by the composition of the iron-antimony oxide but also in order for the iron-antimony oxide to be an effective catalyst, a specific iron-antimony oxide compound ($FeSbO_4$) must be present therein. The atomic ratio of iron to antimony should be within the range of from 10:15 to 10:60. This has been experimentally determined to result in the production of the highest promoter effect and a high conversion to acrylonitrile can be obtained.

This has been confirmed using an X-ray diffraction pattern. The d-values and relative intensities of this iron-antimony oxide compound are as tabulated below.

| $2\theta$ | d | $I/I_o \times 100$ |
|---|---|---|
| 27.2 | 3.28 | 97 |
| 34.9 | 2.57 | 100 |
| 38.7 | 2.33 | 20 |
| 40.2 | 2.24 | 10 |
| 43.6 | 2.07 | 2 |
| 53.2 | 1.72 | 70 |
| 55.9 | 1.64 | 20 |
| 60.2 | 1.54 | 10 |
| 63.3 | 1.47 | 10 |
| 67.4 | 1.39 | 25 |

-continued

| $2\theta$ | d | $I/I_o \times 100$ |
|---|---|---|
| 73.8 | 1.28 | 10 |

Figure 2:
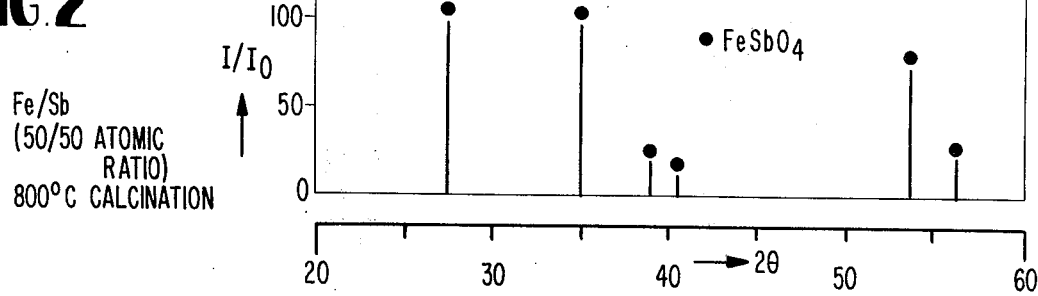
Figure 3:
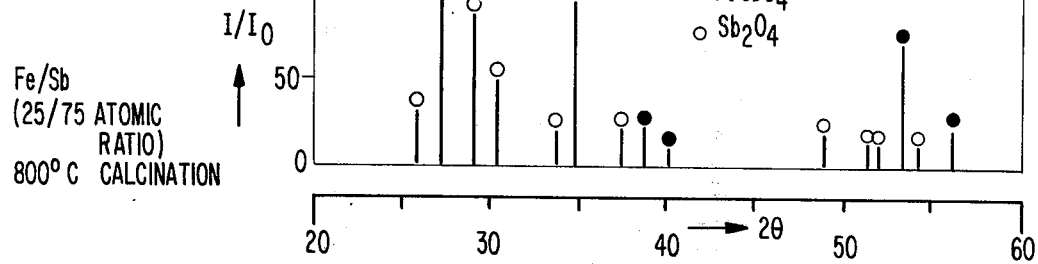
Figure 4:
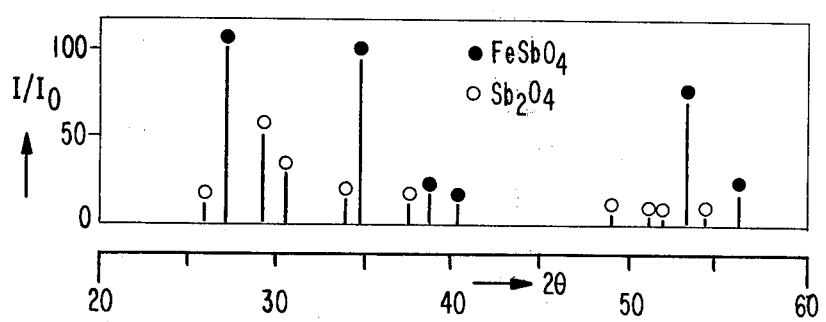
Figure 5:
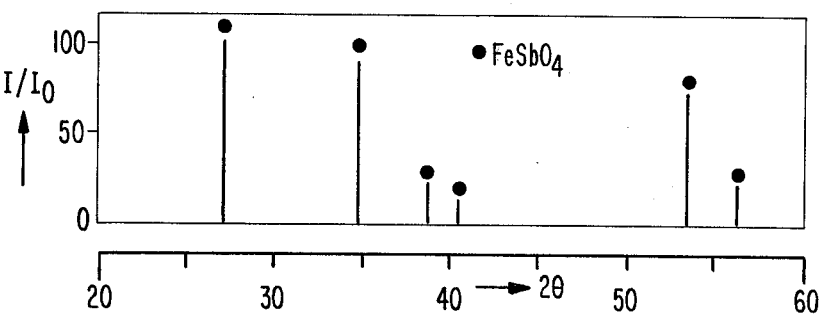

$\theta$: angle of diffraction (Ni filtered Cu K$\alpha$ radiation)
d: lattice spacing
I: intensity of diffraction line
Io: intensity of the most intense diffraction line An X-ray diffraction analysis also demonstrates clearly how the catalyst structure changes by changing the ratio between the iron and the antimony. The X-ray diffraction patterns of catalysts with varying iron and antimony ratios are shown in FIGS. 1 to 3. FIGS. 1, 2 and 3 show X-ray diffraction patterns of catalysts comprising an iron-antimony oxide having an Fe/Sb atomic ratio of 75:25, 50:50 and 25:75, respectively, and obtained by calcining at 800° C. The effective structure as a catalyst for preparing acrylonitrile is $FeSbO_4$ as described above. Where the proportion of iron is high, $\alpha$-$Fe_2O_3$ (shown by the symbol $\Delta$ in FIG. 1) is formed, and where the proportion of antimony is large, $Sb_2O_4$ (shown by the symbol O in FIG. 3) is formed. However, neither $\alpha$-$Fe_2O_3$ nor $Sb_2O_4$ is effective for the formation of acrylonitrile; the $\alpha$-$Fe_2O_3$ increases complete oxidizability (i.e., the formation of $CO_2$), and the $Sb_2O_4$ is inert. In other words, if $Sb_2O_4$ is present in a catalyst, the $Sb_2O_4$ is regarded as an inert material for producing acrylonitrile. But the presence of $\alpha$-$Fe_2O_3$ should be avoided since it reduces the acrylonitrile selectivity. U.S. Pat. No. 3,197,419 briefly discloses the X-ray examination of the catalyst, but does not recognize the importance of the $FeSbO_4$.

In the catalyst composition used in this invention, the Me and Te ingredients are added to the iron-antimony oxide compound in accordance with the composition specified above. the d value of a catalyst composition having these components added is substantially the same as that of the above iron-antimony oxide compound. In addition, this catalyst scarcely shows a diffraction peak of an oxide of any single component thus added or a peak of a newly formed compound, and the diffraction pattern substantially comprises a peak of the iron-antimony oxide compound.

A detailed examination, however, shows that its d value changes, and there is an appreciable change in the lattice constant. This indicates that the above components which are added form a solid solution. This will be specifically described with reference to the X-ray diffraction patterns.

As examples of the catalyst used in this invention, the X-ray diffraction patterns of Catalysts 6, 12, 13 and 17 to be described hereinbelow are shown in FIGS. 4, 5, 6 and 7, respectively. These catalysts exhibit almost the same X-ray diffraction patterns as $FeSbO_4$ shown in FIG. 2, and no oxide or other compound ascribable to the components added is seen. (If oxides consisting of the components added are prepared in the same way as in the Examples given hereinbelow in the absence of an ironantimony oxide, the corresponding oxides, such as vanadium pentoxide, molybdenum trioxide, tungsten trioxide, and tellurium dioxide must be formed.) It has also been found that the lattice constant differes between the iron-antimony oxide compound and the case where the components have been added. The above two points have led to the confirmation that in the catalysts used in this invention, all of the ingredients added are substantially dissolved in the iron-antimony oxide compound.

When the above added components are present as single oxides, they scarcely contribute to the catalytic function of the resulting composition. Especially when the Me components are present in a free state and not in solid solution, they exert adverse effects. For example, comparative catalysts (Catalysts 22 and 26 to be described hereinbelow) in which the components added are present clearly as free oxides as can be seen from the X-ray diffraction patterns in FIGS. 8 and 9 exhibit a low acrylonitrile selectivity.

As set forth above it is essential in the catalyst of this invention that all of the Me and Te components substantially form a solid solution in an iron-antimony oxide compound ($FeSbO_4$).

The condition of the formation of a solid solution can be determined by X-ray diffraction analysis of the catalyst. Where peaks of $FeSbO_4$ are present and no peaks of the free oxides of vanadium, molybdenum and tungsten are present in the X-ray diffraction analysis, a solid solution exists. The X-ray diffraction analysis used to determine such is carried out with an X-ray diffraction apparatus, "D-9C type" (produced by Rigaku Denki Co., Ltd., Japan) under the following conditions.

| | |
|---|---|
| Excitation Potential | : 40 KV, 20 mA |
| Base Line | : 80/1000 |
| Channel Width | : 360/500 |
| Full Scale | : 2000 cps |
| Slit | d.v. 2° |
| | r.s. 0.3° |
| | s.s. 2° |
| Target | : Cu |
| Filter | : Ni |
| Time Constant | : 2 |

A catalyst containing only an iron-antimony oxide as an active ingredient is essentially susceptible to a reducing atmosphere, and attempts to carry out an ammoxidation reaction in a low oxygen concentration using this catalyst results in a reduction in the selectivity of acrylonitrile, and in an extreme case, may cause a permanent degeneration of the catalyst.

U.S. Pat. No. 3,668,147 discloses that catalytic activity in a low oxygen concentration region can be maintained by adding an oxide of at least one metal selected from the group consisting of V, Mo and W; the acrylonitrile selectivity can be increased without substantially affecting the catalyst activity in a low oxygen concentration by adding an oxide of tellurium; and that an oxide of at least one element selected from the group consisting of P and B has an auxiliary activity for the tellurium oxide. In the catalyst used in the present invention, the object of the addition of these components is the same as that described in U.S. Pat. No. 3,668,147, but by the change of the amounts of these components added, the superior effects obtained with these prior catalysts can be obtained and further new and unexpected effects are obtained, i.e., a high acrylonitrile selectivity being maintained even when the proportion of ammonia to propylene is reduced.

In this invention, the amount which is suitable of the Me component, which is at least one selected from the gorup consisting of vanadium, molybdenum and tungsten, is an atomic ratio of more than 1 but not greater than 10, preferably about 1.2 to 10, per 10 of the Fe component. When the amount of the above-described Me component added exceeds 10 to 10 of the Fe component, the acrylonitirle selectivity falls and also difficulty in forming a solid solution results. On the other hand, when the Me component is added in an amount of not more than 1, the Me component more easily forms a solid solution, but the above-described effects cannot be obtained.

The suitable amount of the Te component is an atomic ratio of 0.5 to 10 per 10 of the Fe component. When the Te component is added in a larger amount than 10 per 10 of the Fe component, the reaction rate is reduced and such a catalyst is not practical. On the other hand, when the amount of the Te component is below 0.5 per 10 of the Fe component, the acrylonitrile selectivity decreases.

Further, it is preferred that the R component, i.e., a phosphorus or boron component, is incorporated into the catalyst of this invention. The suitable amount of the R component is an atomic ratio more than 0 but not greater than 5 per 10 of the Fe component. When the amount of the R component exceeds 5 per 10 of the Fe component, the activity of the catalyst is adversely greatly affected. The amount of the R component in the invention is expanded as compared with that employed in U.S. Pat. No. 3,668,147 since the Me component is added in a larger amount to the Fe component.

U.S. Pat. No. 3,716,496 discloses that an iron-antimony oxide-type catalyst having a higher antimony content than iron frequently causes "sticks" (minute thorn-like projections on the surface of the catalyst) composed of antimony oxides (mainly of antimony tetroxide) in the free state in a step of calcining at a high temperature to impart the desired activity. These sticks come off from the catalyst during use and scatter as adhering fine fragments to cause difficulties such as a blockage of pipes; and that the formation of sticks can be prevented by adding a metallic component which reacts with the antimony oxide in the catalyst calcining step and does not impair the catalytic activity of the catalyst.

In the catalysts used in this invention, too, at least one metallic component selected from the group consisting of Cu, Mg, Zn, La, Ce, Al, Cr, Mn, Co, Ni, Bi and Sn as component Q is added. The object of the use of this component is the same as that in U.S. Pat. No. 3,716,496. But, new components such as Cr, Mn, Co, Ni, Bi and Sn are further added as the Q component of this invention instead of the components such as Ag, Be, Ca, Sr, Ba and Cd as employed in U.S. Pat. No. 3,716,496. By the use of the Q component of this invention, not only can sticks be prevented but also the catalytic ability is increased due to a synergistic effect with other catalytic components. That is, the addition of this component also makes it possible to improve the fluidizability of the catalyst, and by selecting the type and amount of this component, the rate of reaction can be adjusted to a suitable value. Further, the addition of this component can be employed to increase the acrylonitrile selectivity.

The suitable amount of the Q component of the catalyst of this invention is an atomic ratio of 0.1 to 10 per 10 of the Fe component. When the amount of the Q component is below the 0.1 per 10 of the Fe component, sufficient stick-preventing effects cannot be obtained. On the contrary, when the amount exceeds 10 per 10 of the Fe component, a high stick-preventing effect is obtained, but the desirable activities of the catalyst, in particular, the acrylonitrile selectivity, is reduced.

As a result of examining the catalyst structures, it has been found that a catalyst comprising a solid solution of the Me and Te components in the iron-antimony oxide compound results in wider compositional ranges of superior catalysts than the range of the composition disclosed in U.S. Pat. No. 3,716,496 and that catalysts of such a structure give rise to an increase in the yield of acrylonitrile, and a decrease in the amount of ammonia consumed, i.e. in the amount of sulfuric acid for neutralization required. It is clear from the results in Table 2 given hereinbelow that when the ratio of the Me component is $1.2 \leqq c \leqq 5$, the conversion of propylene to acrylonitrile approaches as high as about 80% or more.

The catalysts used in this invention can be prepared by any methods known in the art so long as the catalysts obtained have the catalyst structure and composition as specified above. For example, when a catalyst for use in a fluidized bed is to be prepared, a slurry prepared from the catalyst components is spray dried by a suitable means. Alternatively, a slurry prepared from iron and antimony components is first spray dried to form an ironantimony oxide base catalyst, and then an aqueous solution of the additional components to be added is sprayed onto the base catalyst or impregnated into the base catalyst to prepare a final catalyst composition. Of course, it is possible to form a carrier-supported catalyst by mixing a carrier with the slurry. A catalyst for use in a fixed bed can be prepared by drying a slurry prepared from the catalyst components, kneading the slurry, and then molding the mixture into a cylindrical or spherical shape. By incorporating a carrier in the slurry, a carrier-supported catalyst can also be prepared.

The starting material for each of the components comprising the catalyst can be selected from a number of types such as the oxides, hydroxides, chlorides and nitrates of the respective components.

The starting material for the iron component of this catalyst can be selected from many types, for example, ferrous oxide, ferric oxide or iron ferroferric oxide ($Fe_3O_4$). Compounds which are finally stabilized as an iron oxide after a chemical treatment or calcining treatment can be used. Such compounds include, for example, inorganic iron salts such as iron nitrate or iron chloride, or organic acid iron salts such as iron acetate or iron oxalate. These compounds can be neutralized with alkalis such as ammonia to form hydroxylated iron salts and then calcined, or can be directly calcined to form oxides. Also, iron hydroxide and a solution of metallic iron in nitric acid can be used. Regardless of which starting material is chosen, the starting material is preferably added in a form such as a fine powder, an aqueous solution or a sol since intimate mixture with the other components is important.

The starting material for the antimony component can be antimony oxides such as antimony trioxide, antimony tetroxide or antimony pentoxide. Compounds which are finally stabilized as an oxide of antimony after a chemical treatment or calcining treatment can also be used. For example, products obtained by oxidizing metallic antimony or various antimony hydroxides with nitric acid can also be used. Also, readily hydrolyzable antimony salts and antimony halides such as antimony trichloride or antimony pentachloride can also be used. These antimony halides are hydrolyzed with water to form hydrous oxides. Since antimony halides are volatile at high temperatures, it is preferred to hydrolyze the antimony halides before the calcining step. In order to obtain an intimate mixing with the other components, the same care as in the case of the iron component is required.

All water-soluble or water-insoluble vanadium compounds can be used as a starting material for the vanadium component. For example, vanadium pentoxide, ammonium metavanadate, vanadyl oxalate or vanadium halides can be used.

All water-soluble or water-insoluble molybdenum compounds can be used as a starting material for the molybdenum component. For example, molybdenum trioxide, molybdic acid, ammonium paramolybdate, ammonium metamolybdate or molybdenum halides can be used.

With respect to the tungsten component, the same can be said as in the case of the molybdenum component.

The tellurium component can be any water-soluble or water-insoluble tellurium compounds, such as tellurium dioxide, tellurous acid or telluric acid. Metallic tellurium can also be used. The metallic tellurium can be used in the form of a powder, or after reaction with hot nitric acid.

The starting material for the "anti-stick" components, that is, Cu, Mg, Zn, La, Ce, Al, Cr, Mn, Co, Ni, Bi and Sn can be selected from many types of compounds. Preferably, the starting materials for these metal components are their oxides, hydroxides, nitrates and chlorides.

In the case of copper, cupric nitrate or metallic copper dissolved in nitric acid is preferably used. Copper hydroxide obtained by the hydrolysis of cupric chloride and cupric oxide can also be used.

As the magnesium component, magnesium nitrate is preferably used. Magnesium hydroxide and magnesium oxide dissolved in nitric acid can also be used.

Zinc nitrate and bismuth nitrate are preferably used as starting materials for the zinc and bismuth components, respectively. Commercially available compounds can be used or metallic zinc or bismuth dissolved in nitric acid can be used. Zinc chloride, bismuth chloride, or the hydrolyzed products thereof can also be used.

In the case of lanthanum and cerium, nitrate salts of these components can suitably be used. The oxides of lanthanum and cerium can also be used.

The preferred starting material for the aluminum component is aluminum hydroxide obtained by hydrolysis of sodium aluminate with an acid, or by hydrolysis of aluminum sulfate or aluminum chloride with a base. Metallic aluminum and aluminum nitrate can also be used as a starting material for the aluminum component.

The starting material for the chromium component includes chromium nitrate, chromium hydroxide, chromium oxide and chromic anhydride.

In the case of manganese, cobalt and nickel, the nitrates, hydroxides and oxides of manganese, cobalt and nickel can be used.

In the case of tin, stannous oxide and stannic oxides are preferred. Tin hydroxide obtained by the hydrolysis of a tin halide such as stannous chloride or stannic chloride or metallic tin oxidized with nitric acid can also be used.

Phosphoric acid and boric acid are the most convenient starting materials for the phosphorus component and the boron component.

Care must be exercised in preparing the catalyst used in this invention because the Me component and the Te component must form a solid solution with the iron-antimony oxide compound. Specifically, a slurry prepared from the starting material components of the catalyst must be very thoroughly homogenized. Accordingly, raw materials for the catalyst components are preferably soluble materials. Where soluble materials are not available, the use of materials having high reactivity is preferred. When insoluble materials are used, they are preferably reduced to as fine a particle size as is possible prior to addition. In particular, because the bonded condition of V, Mo, W and Te in the catalyst is important to the performance of the resulting catalyst, soluble compounds are used as their raw materials in order to avoid any difficulty. The use of compounds such as oxides which have low reactivity preferably should be avoided. Needless to say, the individual materials are well mixed in the slurry prepared, and their dispersed condition should be maintained as well as possible. When drying the slurry prepared, care must be taken so that the individual components are uniformly distributed in the dried product.

The catalyst of this invention can be used without carriers, and exhibits excellent performance in such a case also. The catalyst can also be used supported on a suitable carrier. Preferably, the amount of the carrier is about 10% by weight to about 90% by weight based on the total weight of the catalyst. Many known carriers for catalysts can be used. Specific examples of carriers are silica, alumina, titania, zirconia, silica-alumina, and Alundum. Of these, silica is especially preferred.

A high level of activity is imparted to the catalyst of this invention by heating the catalyst at high temperatures (i.e., calcining the catalyst) after mixing the ingredients and drying the mixture. All of the individual starting materials can be mixed initially, or all or some of the additional ingredients can be added after drying or calcining. In any case, the catalyst finally obtained should have the composition and structure as specified above.

The calcining conditions are very important in the activation of the catalyst. The optimum calcination conditions can vary depending on the composition of the catalyst and the method of catalyst preparation. However, preferably, calcination is performed for about 1 to about 50 hours at a temperature of from about 200° C. to about 600° C., and then finally for about 1 to about 50 hours at a temperature of from about 500° C. to about 900° C. The choice of the final calcining conditions is extremely important, and if the calcining conditions are different, catalysts of the same composition show varying catalytic activities. Especially when the proportions of V, Mo, W and Te components are large, calcining temperatures, which are too high result in the formation of crystals of the free oxides of these components, and therefore, result in reduced catalytic activities. The optimum calcining conditions should be selected within the above range depending on the composition of the individual catalysts. Employment of calcining temperatures above 950° C. should be avoided with any composition.

When the process of this invention is performed using a fluidized-bed reactor, the catalyst used for this process is preferably prepared by the method disclosed in U.S. Pat. Nos. 3,657,155 or 3,686,138.

In the process of this invention, not only substantially pure propylene, but also a mixture of propylene with a paraffinic hydrocarbon such as ethane, propane or butane can be used.

Oxygen can be used in this invention in any form, but for economic reasons, air is preferred. Air can be used diluted with an inert gas, or enriched appropriately with oxygen. In the production of acrylonitrile, it is sometimes the practice to increase the partial pressure of propylene so as to increase the productivity. Usually, however, this results in a reduction in the acrylonitrile selectivity. The acrylonitrile selectivity is not, however, significantly reduced with the catalyst used in this invention, and therefore, the catalyst provides the advantage that the process of this invention can be performed at an elevated partial pressure of propylene (effected by a reduction in the partial pressure of nitrogen) by using air enriched with oxygen.

A suitable molar ratio of oxygen/propylene in the material to be fed to the reactor in performing the process of this invention is about 1:1 to about 4:1. Because the catalyst used in this invention exhibits high acrylonitrile selectivity, relatively low oxygen/propylene ratios, that is, within the range of about 1.5:1 to about 2.5:1, are preferred. As a result of reducing the oxygen/propylene molar ratio (that is, reducing the amount of air used), the output (space time yield) of acrylonitrile per unit hour per unit volume of the reactor (that is, productivity) can be greatly increased. The catalyst used in this invention is a significant technical advance over conventional catalysts, for example, those described in U.S. Pat. No. 3,716,496, in that the catalyst provides high acrylonitrile selectivity, and superior catalytic activity is maintained even when the partial pressure of oxygen is low.

The ammonia/propylene molar ratio of the materials to be fed to the reactor can be varied within the range of about 0.8:1 to about 3:1, preferably about 0.9:1 to about 1.5:1. With the catalyst of this invention, substantially no combustion of ammonia under the actual ammoxidation conditions in the presence of propylene occurs, although in the absence of propylene (that is, when only ammonia and air are present) ammonia might be oxidized and decomposed (that is, combustion). In addition, this catalyst does not give rise to an increase in the amounts of by-products as in the case of conventional catalysts. In this case, the amount of HCN formed slightly decreases and acrolein is formed in only a very slight amount; there is no appreciable formation of acrylic acid. Accordingly, in the present invention, it is substantially consequential to use ammonia in excess. It is preferred to adjust the molar ratio of ammonia/propylene to be fed into the reactor to a range of about 0.9:1 to about 1.15:1. By reducing the proportion of ammonia to be fed, the amount of the unreacted ammonia flowing out of the reactor and remaining in the reaction gas can be decreased. Consequently, the amount of acid (usually sulfuric acid) used for neutralizing the ammonia in the off-gas can be reduced. Furthermore, this results in a reduced amount of ammonium salts (usually, ammonium sulfate) contained in the waste liquor from acrylonitrile-manufacturing facilities, and therefore, facilitates the treatment of the waste water. The catalyst used in this invention exhibits a greater technical advance than the conventional catalysts, for example, those described in U.S. Pat. No.

3,716,496, in that not only does the catalyst of this invention exhibit a high acrylonitrile selectivity, but also the catalyst maintains its superior catalytic activity even when the partial pressure of ammonia is low.

Since the catalyst of this invention does not cause ammonia to burn, the amount of oxygen consumed is small in this respect also. Accordingly, the oxygen/propylene molar ratio and the oxygen/ammonia molar ratio in the feed materials can be reduced, and the productivity of acrylonitrile is greatly improved. When ammonia is burned, the formation of nitrogen oxides ($NO_x$) poses a problem in relation to air pollution. The catalyst of this invention, which does not cause a combustion of ammonia, is quite free from this problem.

Attempts have often been made to supply water to the reaction system in order to increase the selectivity of the final product (in an ammmoxidation reaction, further in order to inhibit the combustion of ammonia) in a vapor-phase catalytic oxidation or an ammoxidation reaction. There have been many examples of water addition in the ammoxidation of propylene, also. In the present invention, however, the addition of water, which is disadvantageous for reasons of both energy requirements and operation, is substantially unnecessary since the catalyst of this invention does not cause a combustion of ammonia, and can exhibit a sufficiently high acrylonitrile selectivity without the addition of water. Water, however, can be added as desired because a small amount of water sometimes has an effect of inhibiting the formation of byproducts, especially carbon dioxide gas to some extent. In such a case, the amount of water is up to 2 molar times that of the propylene fed.

The composition of the feed gaseous mixture described above is that of the total of the gases that have been fed into the reactor. The feed gases can be fed portionwise to the reactor, if desired.

In the performance of the process of this invention, a suitable reaction temperature is about 380° C. to about 500° C., preferably about 400° C. to about 470° C.

A suitable reaction pressure is a pressure in the vicinity of normal atmospheric pressure to about 3 Kg/cm²-G, preferably from a pressure in the vicinity of normal atmospheric pressure to about 2 Kg/cm²-G. With the catalyst of this invention, too, the acrylonitrile selectivity slightly decreases as the reaction pressure increases, but the rate of decrease is less than in the case of conventional catalysts. In this regard also, the catalyst of this invention shows an improvement over conventional catalysts.

The apparent contact time is suitably within the range of about 1 to about 30 seconds, preferably about 2 to about 20 seconds.

However, if a certain catalyst exhibits superior performance in an early stage of commercial operation, the catalyst cannot be considered a superior commercial catalyst unless its performance under economical reaction conditions lasts for prolonged periods of time. In this regard, also, the catalyst used in this invention can maintain its high performance for long periods of time under severe reaction conditions as compared with conventional catalysts, for example, those described in U.S. Pat. No. 3,716,496.

Any type of apparatus conventionally used for vapor-phase catalytic reactions can be employed for performing the process of this invention. The catalyst layer can be a fixed bed or a fluidized bed.

The reaction product can be recovered using any desired method known in the art. One example of a method of recovery involves washing the off-gas from the reactor with cold water or a solvent suitable for extraction of acrylonitrile to separate the desired acrylonitrile and also HCN and acetonitrile, etc., from the off-gas, and then separating and recovering the acrylonitrile.

The following Examples and Comparative Examples are given to illustrate embodiments and advantages of this invention more specifically. Unless otherwise indicated herein, all parts, percents, ratios and the like are by weight.

The yields and selectivities of the products, as referred to in the present specification, were determined as follows:

$$\text{Conversion of Propylene (\%)} = \frac{\text{Carbon Weight of the Product}}{\text{Carbon Weight of Starting Propylene Fed}} \times 100$$

$$\text{Selectivity (\%)} = \frac{\text{Carbon Weight of the Product}}{\text{Carbon Weight of the Propylene Reacted}} \times 100$$

Activity tests on catalysts were performed as follows:

CATALYST ACTIVITY TEST METHOD

Test Method 1: Test in a fixed bed-type reactor

A catalyst sample was filled in a U-shaped reactor having an inside diameter of 16 mm so as to provide a predetermined contact time. The reactor was heated using a mixture of equal amounts of sodium sulfite and potassium nitrate. A gaseous mixture of propylene, ammonia and air in which the $O_2$/propylene molar ratio was about 2.2 and the $NH_3$/propylene molar ratio was about 1.15 was fed into the reactor at a rate of 10 liters (NTP) per hour. The reaction pressure was atmospheric pressure. The reaction products were quantitatively analyzed by gas-chromatography.

Test Method 2: Test in a fluidized-bed reactor

Using a fluidized-bed reactor in which the catalyst fluidizing portion had an inside diameter of 2 inches and a height of 2 meters, a gaseous feed mixture (consisting of propylene, ammonia and air) was fed so that the apparent linear velocity of the gases was 15 cm/sec. The reaction conditions were varied according to the purpose. The reaction products were collected, and quantitatively analyzed by gas-chromatography. $NH_3$ and HCN were quantitatively analyzed to a titration method.

PREPARATION OF CATALYSTS

Catalysts were prepared by the following methods. Catalysts 1 to 18 were catalysts in accordance with this invention, and Catalysts 19 to 27 were comparative catalysts prepared in order to clarify the significance of the present invention.

CATALYST 1

A catalyst having the empirical formula

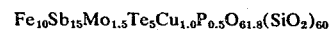

$Fe_{10}Sb_{15}Mo_{1.5}Te_5Cu_{1.0}P_{0.5}O_{61.8}(SiO_2)_{60}$ was prepared as follows:

28.0 g of electrolyzed iron powder and then 32.0 g of metallic tellurium were added portionwise to a liquid consisting of 309 ml. of nitric acid (specific gravity: 1.38) and 410 ml. of water. To the resulting solution were added 12.1 g of copper nitrate [(Cu(NO₃)₂.6-H₂O] and then 2.9 g of phosphoric acid (purity: 85%) to form a Solution (I).

13.3 g of ammonium molybdate [(NH₄)₆Mo₇O₂₄.4-H₂O )] was dissolved in 904 g of silica sol (SiO₂ content 20% by weight) by heating to form Solution (II).

Solutions (I) and (II) were mixed, and 109.7 g of powdery antimony trioxide was added.

The resulting suspension was treated with 15% aqueous ammonia solution to adjust the pH to 3. With good stirring, the suspension was heated under reflux at 100° C., and dried. The dried product was calcined for 2 hours at 200° C. and for 2 additional hours at 400° C. Then, water was added and kneaded with the calcined product. The product was then molded into cylindrical articles each having a length of 2 mm and a diameter of 2 mm, followed by further calcining for 4 hours at 700° C.

CATALYSTS 2 TO 11, CATALYSTS 14 TO 19, AND CATALYSTS 22 to 24 were prepared in the same way as in the above preparative procedure for Catalyst 1. The compositions of these catalysts and the final calcining conditions are shown in Table 1.

The starting materials used were ammonium metavanadate for the V component, ammonium paramolybdate for the Mo component, ammonium paratungstate for the W component, metallic tellurium oxidized with nitric acid, and tellurium dioxide or telluric acid for the Te component. As for the Q component, nitrate salts were used for each of the Cu, Zn, La, Ce, Al, Cr, Mn, Co, Ni and Bi components; hydroxides dissolved in nitric acid were used for each of the Mg and Al components; and metallic tin oxidized with nitric acid was used for the Sn component.

3.2 liters of nitric acid (specific gravity: 1.38) was mixed with 2 liters of water. 0.447 Kg of electrolyzed iron powder was added portionwise to the mixture, and then 0.932 Kg of cobalt nitrate was added to form Solution (II).

105 g of ammonium tungstate and 170 g of ammonium molybdate were dissolved in 920 ml. of water, and 552 g of telluric acid was added to form Solution (III).

49 g of boric acid was dissolved in 9.61 Kg of silica sol (Ludox HS, a product of Du Pont: SiO₂ content 30% by weight) to form Solution (IV).

Solutions (III) and (II) and Compound (I) were added in this order to Solution (IV), and with good stirring, a 15% aqueous ammonia solution was added portionwise to adjust the pH of the solution to 2.0. With thorough stirring, the solution was heated at 100° C. for 8 hours. The resulting slurry was conditioned to a concentration (calculated as the oxides) of about 20%, and spray dried. The resulting fine spherical particles were calcined for 8 hours at 250° C., and for 16 additional hours at 400° C., and finally for 4 hours at 700° C.

CATALYST 13

A catalyst having the empirical formula

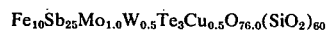

$Fe_{10}Sb_{25}Mo_{1.0}W_{0.5}Te_3Cu_{0.5}O_{76.0}(SiO_2)_{60}$ was prepared in the same way as in the preparative method for Catalyst 12. Copper nitrate was used as the material for the Cu component, and the final calcination was carried out at 710° C. for 4 hours.

CATALYST 20

A catalyst having the empirical formula

Table 1

| Catalyst | Composition (atomic ratio) | | | | | | Final Calcining Conditions | |
|---|---|---|---|---|---|---|---|---|
| | Fe | Sb | Me | Te | Q | R | Si | Temperature (° C) | Time (Hrs.) |
| 2 | 10 | 25 | V₂ | 10 | Mg₂ | B | 30 | 680 | 4 |
| 3 | 10 | 60 | V₀.₅Mo₀.₅W₀.₅ | 5 | Zn₃ | — | 30 | 700 | 4 |
| 4 | 10 | 25 | W₁.₅ | 4 | La₁ | — | 30 | 680 | 4 |
| 5 | 10 | 60 | Mo₄ | 5 | Cu₅ | — | 30 | 700 | 4 |
| 6 | 10 | 60 | W₂ | 5 | Mg₅ | — | 30 | 700 | 4 |
| 7 | 10 | 60 | V₁Mo₂ | 8 | Zn₂Al₁ | — | 30 | 640 | 3 |
| 8 | 10 | 60 | Mo₂ | 5 | La₀.₅Ce₁ | — | 30 | 660 | 4 |
| 9 | 10 | 25 | Mo₂ | 4 | Al₃ | — | 60 | 690 | 4 |
| 10 | 10 | 25 | W₁Mo₁ | 4 | Cr₂ | — | 60 | 670 | 4 |
| 11 | 10 | 25 | W₁Mo₀.₂₅ | 2 | Mn₂Al₁ | — | 60 | 750 | 3 |
| 14 | 10 | 30 | V₀.₁Mo₁.₅ | 4 | Cu₂Ni₂ | — | 60 | 730 | 4 |
| 15 | 10 | 30 | V₀.₂Mo₁W₀.₂ | 3 | Bi₃ | — | 60 | 740 | 2 |
| 16 | 10 | 25 | W₀.₅Mo₀.₇ | 3 | Sn₃ | P₁ | 60 | 780 | 2 |
| 17 | 10 | 15 | V₀.₁Mo₆ | 10 | Zn₂ | P₁B₂ | 60 | 620 | 3 |
| 18 | 10 | 35 | Mo₉ | 10 | Al₁ | B₁ | 80 | 600 | 3 |
| 19 | 10 | 25 | W₀.₂₅ | 0.5 | — | — | 30 | 900 | 2 |
| 22 | 10 | 25 | Mo₁₅ | 1 | — | — | 60 | 600 | 4 |
| 23 | 10 | 25 | Mo₀.₁W₀.₁ | 0.5 | Cr₂ | — | 850 | 4 | |
| 24 | 10 | 25 | W₀.₅ | 2 | Mn₂Al₁ | — | 60 | 750 | 3 |

CATALYST 12

A catalyst having the empirical formula $Fe_{10}Sb_{25}W_{0.5}Mo_{1.2}Te_3Co_4B_1O_{81.6}(SiO_2)_{60}$ was prepared by the following method.

2.92 Kg of powdery antimony trioxide (particle size: less than 20 microns), compound (I), was weighed out.

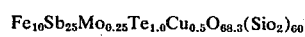

$Fe_{10}Sb_{25}Mo_{0.25}Te_{1.0}Cu_{0.5}O_{68.3}(SiO_2)_{60}$ was prepared in the same way as in the preparative method for Catalyst 13. The final calcination was carried out at 710° C. for 4 hours.

CATALYST 21

A catalyst having the empirical formula $Fe_{10}Sb_{25}Te_3Co_4O_{75}(SiO_2)_{60}$ was prepared in the same way as in the preparative method for Catalyst 12. The final calcination was carried out at 750° C. for 4 hours.

CATALYST 25

A catalyst having the empirical formula $Fe_{10}Sb_{25}W_{0.8}Te_3Co_4B_1O_{78.9}(SiO_2)_{60}$ was prepared in the same way as in the preparative method for Catalyst 12. The final calcination was carried out at 710° C. for 4 hours.

CATALYST 26

A catalyst having the empirical formula $Fe_{10}Sb_{60}W_2Te_5Mg_5O_{156}(SiO_2)_{30}$ was prepared as follows:

28.0 g of electrolyzed iron powder and then 32.0 g of metallic tellurium were added portionwise to a liquid consisting of 309 ml. of nitric acid (specific gravity: 1.38) and 410 ml. of water to completely dissolve these components. 23.2 g of powdery tungsten trioxide was added to the resulting solution. On the other hand, 64.3 g of magnesium nitrate was dissolved in 904 g of silica sol (SiO$_2$ content 20% by weight).

These solutions were mixed, and 438.5 g of powdery antimony trioxide was added. The mixture was dried, and calcined for 2 hours at 200° C. and 2 additional hours at 400° C. The calcined product was kneaded with water, and molded into cylindrical articles having a length of 2 mm and a diameter of 2 mm. The molded articles were then calcined at 700° C. for 4 hours.

CATALYST 27

A catalyst having the empirical formula $Fe_{10}Sb_{15}V_{0.1}Mo_6Te_{10}Zn_2P_1B_2O_{90.8}(SiO_2)_{60}$ was prepared as follows:

2.91 Kg of powdery antimony trioxide, Compound (I), (particle size: less than 20 microns) was weighed out.

3.2 liters of nitric acid (specific gravity: 1.38) was mixed with 2 liters of water and the mixture was heated. 0.743 Kg of electrolyzed iron powder was added portionwise to the solution, and zinc nitrate was added to form Suspension (II).

13 g of vanadium pentoxide and 1.15 Kg of molybdenum trioxide were taken (III).

3.06 Kg of telluric acid, 153 g of phosphoric acid (purity 85%) and 164 g of boric acid were dissolved in 16.0 Kg of silica sol (Ludox HS, a product of Du Pont: SiO$_2$ content 30% by weight) to form a Solution (IV).

(III), (II) and (I) were added in this order to (IV), and the mixture was dried at 120° C. for 16 hours, and then calcined for 2 hours at 250° C. and for 2 additional hours at 400° C. and finally for 3 hours at 620° C.

ACTIVITY TESTS

1. Catalysts 1 to 11, 14, to 19, 22 to 24, 26 and 27 were tested by Method 1 described above. The results obtained are shown in Table 2.

It can be seen from the results obtained that Catalyst 1 to 18 of this invention have better performance than Catalysts 19 to 27 for comparison.

Catalysts 19 is an example which is outside of this invention because the Me component is less than the amount specified in this invention and corresponds to that of U.S. Pat. No. 3,668,147, Example 1.

Catalyst 22 has a larger proportion of Me than the catalyst of this invention. In this case, MoO$_3$ is present in the free state, as can be seen from the X-ray diffraction pattern shown in FIG. 8.

Catalysts 23 to 24 have a smaller proportion of Me than the catalyst of this invention and varied proportions of Q components. All of these catalysts exhibited inferior results to the catalysts of this invention.

Catalyst 26 has a composition within the atomic range specified in this invention, but the WO$_3$ as the Me component is present in the free state and not in a solid solution as is required for the catalyst of this invention. Accordingly, this catalyst is not within the scope of this invention. A comparison of this catalyst with Catalyst 6 of this invention which has the same composition clearly shows the significant advantage of the catalyst of this invention.

Catalyst 27 also has the same composition as Catalyst 17 of this invention, but the MoO$_3$ as the Me component is present in the free state and is not in a solid solution as required for the catalyst of this invention.

It is clear from the results in Table 2 that the acrylonitrile selectivities of Catalysts 22, 26 and 27, in which the Me components are present as the free oxides, ranged from 50 to 70%, and were markedly reduced. Further, Catalysts 19, 23 and 24, in which the Me components were added in an amount smaller than in the catalysts of this invention, exhibited acrylonitrile conversions of 75 to 78% and acrylonitrile selectivities of 78 to 82%. On the contrary, Catalysts 1 to 18 of this invention exhibited acrylonitrile conversions of 79 to 85% and acrylonitrile selectivities of 82 to 87%, and it can be said that the catalysts of this invention are superior as compared with the prior art catalysts as described above.

2. Catalysts 12, 13, 20, 21 and 25 were tested by Method 2 described above. The results obtained are shown in Table 3 and also illustrated in FIGS. 10 to 13.

Catalysts 12 and 13 are within the scope of the present invention.

Catalyst 20 has a smaller proportion of the Me component (the catalyst shown in Example 13 of U.S. Pat. No. 3,716,496). Catalyst 21 does not contain the Me component. Catalyst 25 has a smaller proportion of the Me component.

Figure 10:
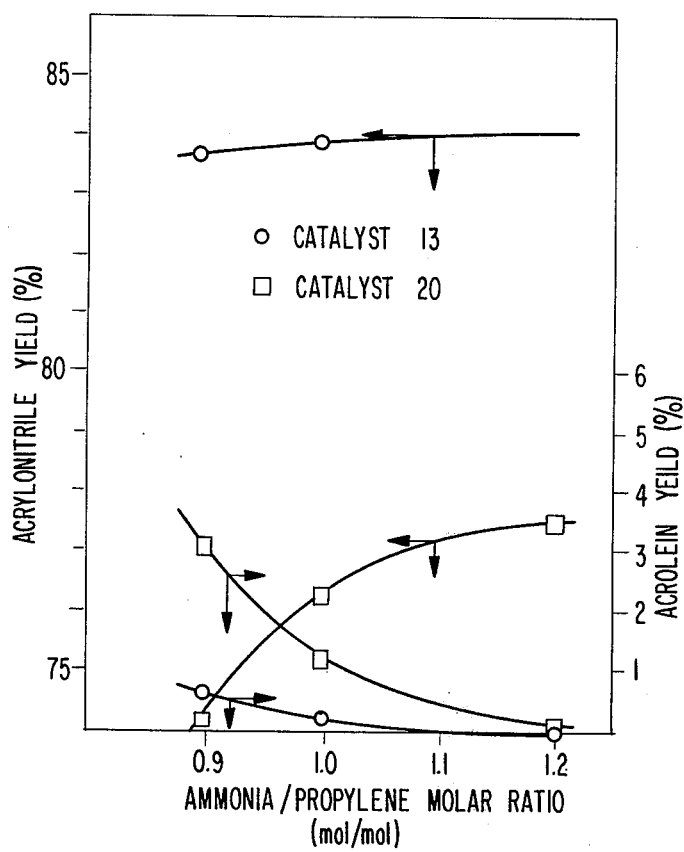
FIGS. 10, 11, 12 and 13 show the evaluations of catalytic activity for catalysts of the invention and comparative catalysts employed in the examples.

The influences of the NH$_3$/C$_3$H$_6$ molar ratio between Catalyst 13 of this invention and Comparative Catalyst 20 are shown in Table 3 and FIG. 10. As is clear from FIG. 10, Catalyst 13 exhibited a higher acrylonitrile yield than that of Catalyst 20, and also, even when the NH$_3$/C$_3$H$_6$ molar ratio dropped, it was possible with Catalyst 13 to maintain the high acrylonitrile yield and to form only a small amount of by-products.

Figure 11:
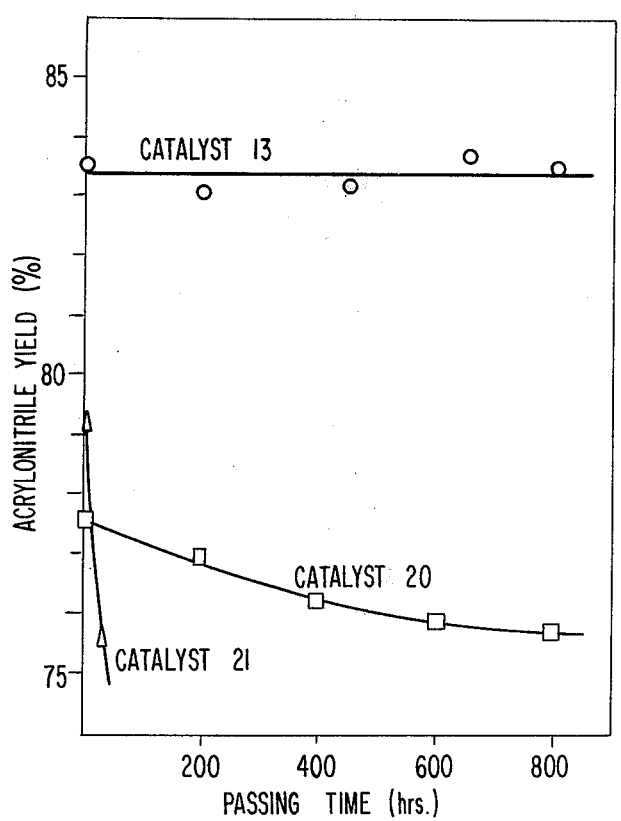

Further, Catalyst 13 of this invention was used for a long period of time under comparatively severe conditions such as an NH$_3$/C$_3$H$_6$ molar ratio of 1.05 and an air/C$_3$H$_6$ molar ratio of 9.6, and when compared with Comparative Catalysts 20 and 21, which were used for a long period of time under slightly less severe conditions such as an NH$_3$/C$_3$H$_6$ molar ratio of 1.10 and air/C$_3$H$_6$ molar ratios of 10.1 and 10.5, respectively. The results obtained are shown in FIG. 11. As is clear from the above results, the catalysts of this invention can maintain a high acrylonitrile yield over a long period of time even at a low $NH_3/C_3H_6$ molar ratio and a low air/$C_3H_6$ molar ratio.

Figure 12:
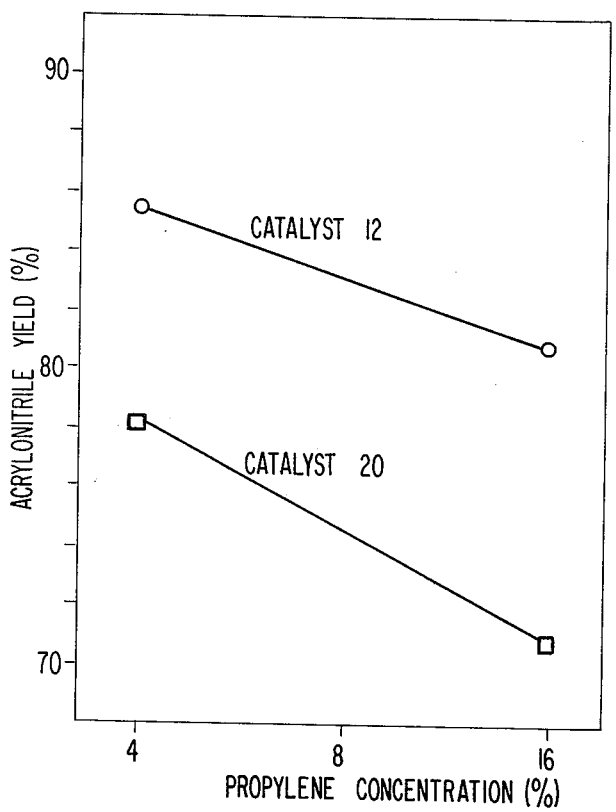

Moreover, the influence upon the propylene concentration between Catalyst 12 of this invention and Comparative Catalyst 20 are shown in Table 3 and FIG. 12. It is noted from these results that Catalyst 12 was less influenced by the increase of the propylene concentration than Catalyst 20.

Figure 13:
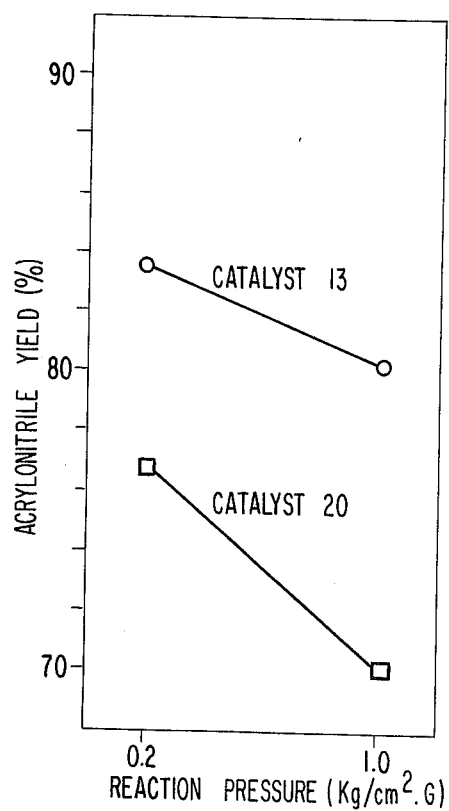

Still further, the influences upon the reaction pressure between Catalyst 13 of this invention and Comparative Catalyst 20 are shown in FIG. 13. It is noted from FIG. 13 that Catalyst 13 was less influenced by the increase of the reaction pressure than Catalyst 20.

Accordingly, it can be said that the catalysts of this invention not only provide a high acrylonitrile yield but also have the following advantages:

1. A high acrylonitrile yield can be obtained and a small amount of by-products such as acrylic acid and acrolein can be formed, even when the $NH_3/C_3H_6$ molar ratio is reduced.
2. A high acrylonitrile selectivity can be obtained, even when the air/$C_3H_6$ molar ratio is reduced.
3. Superior properties can be maintained over a long period of time, even when the $NH_3/C_3H_6$ molar ratio and the $O_2/C_3H_6$ molar ratio are reduced.
4. The decrease in the acrylonitrile selectivity is small, even when the propylene concentration is increased.
5. The decrease in the acrylonitrile selectivity is small, even when the reaction pressure is increased.

Table 2

| Catalyst | Composition (atomic ratio) | | | | | | Reaction Conditions | | Results | | | | |
|---|---|---|---|---|---|---|---|---|---|---|---|---|---|
| | Fe | Sb | Me | Te | O | R | Si | A) (°C) | B) (Sec) | $C_3H_6$ Conversion | | | (%) |
| | | | | | | | | | | AN | $CH_3CN$ | HCN | C) (%) | D) (%) |
| 1  | 10 | 15 | $Mo_{1.5}$ | 5 | $Cu_1$ | $P_{0.5}$ | 60 | 440 | 3.8 | 80 | 0.6 | 5 | 98 | 82 |
| 2  | 10 | 25 | $V_2$ | 10 | $Mg_2$ | $B_2$ | 30 | 420 | 3.2 | 81 | 0.2 | 3 | 97 | 84 |
| 3  | 10 | 60 | $V_{0.5}Mo_{0.5}W_{0.5}$ | 5 | $Zn_3$ | — | 30 | 430 | 4.2 | 82 | 0.4 | 4 | 99 | 83 |
| 4  | 10 | 25 | $W_{1.5}$ | 4 | $La_1$ | — | 30 | 430 | 4.2 | 81 | 0.6 | 6 | 97 | 84 |
| 5  | 10 | 60 | $Mo_4$ | 5 | $Cu_5$ | — | 30 | 420 | 2.1 | 80 | 1.2 | 7 | 95 | 84 |
| 6  | 10 | 60 | $W_2$ | 5 | $Mg_5$ | — | 30 | 450 | 3.0 | 81 | 0.7 | 6 | 98 | 83 |
| 7  | 10 | 60 | $V_1Mo_2$ | 8 | $Zn_2Al_1$ | — | 30 | 420 | 2.1 | 82 | 0.2 | 5 | 95 | 86 |
| 8  | 10 | 60 | $Mo_2$ | 5 | $La_{0.5}Ce_1$ | — | 30 | 420 | 2.1 | 83 | 0.4 | 6 | 98 | 85 |
| 9  | 10 | 25 | $Mo_2$ | 4 | $Al_3$ | — | 60 | 420 | 2.1 | 83 | 0.2 | 5 | 97 | 86 |
| 10 | 10 | 25 | $W_1Mo_1$ | 4 | $Cr_2$ | — | 60 | 430 | 2.8 | 82 | 0.4 | 6 | 98 | 84 |
| 11 | 10 | 25 | $W_1Mo_{0.25}$ | 2 | $Mn_2Al_1$ | — | 60 | 430 | 2.8 | 83 | 0.2 | 5 | 99 | 84 |
| 14 | 10 | 30 | $V_{0.1}Mo_{1.5}$ | 4 | $Cu_2Ni_2$ | — | 60 | 420 | 4.3 | 85 | 0.0 | 3 | 98 | 87 |
| 15 | 10 | 30 | $V_{0.2}Mo_1W_{0.2}$ | 3 | $Bi_3$ | — | 60 | 430 | 2.8 | 84 | 0.3 | 5 | 99 | 85 |
| 16 | 10 | 25 | $W_{0.5}Mo_{0.7}$ | 3 | $Sn_3$ | $P_1$ | 60 | 440 | 3.8 | 84 | 0.6 | 4 | 99 | 85 |
| 17 | 10 | 15 | $V_{0.1}Mo_6$ | 10 | $Zn_2$ | $P_1B_2$ | 60 | 410 | 2.3 | 79 | 1 | 5 | 94 | 84 |
| 18 | 10 | 35 | $Mo_9$ | 10 | $Al_1$ | $B_1$ | 80 | 400 | 2.1 | 79 | 1 | 3 | 94 | 84 |
| 19 | 10 | 25 | $W_{0.25}$ | 0.5 | — | — | 30 | 440 | 5.8 | 78 | 1 | 4 | 95 | 82 |
| 22 | 10 | 25 | $Mo_{15}$ | 1 | — | — | 60 | 420 | 2.0 | 47 | 0.5 | 10 | 86 | 55 |
| 23 | 10 | 25 | $Mo_{0.1}W_{0.1}$ | 4 | $Cr_2$ | — | 60 | 450 | 5.2 | 75 | 0.6 | 6 | 96 | 78 |
| 24 | 10 | 25 | $W_{0.5}$ | 2 | $Mn_2Al_1$ | — | 60 | 450 | 5.2 | 76 | 1.2 | 7 | 94 | 81 |
| 26 | 10 | 60 | $W_2$ | 5 | $Mg_5$ | — | 30 | 420 | 3.5 | 62 | 2 | 9 | 89 | 70 |
| 27 | 10 | 15 | $V_{0.1}Mo_6$ | 10 | $Zn_2$ | $P_1B_2$ | 60 | 400 | 2.1 | 59 | 1 | 7 | 87 | 68 |

Notes:
A) Temperature
B) Contact Time
C) Total Conversion of $C_3H_6$
D) Acrylonitrile Selectivity Table 3

| Catalyst | Reaction Conditions Molar Ratio of Feed Gases | | | | | $C_3H_6$ Concentration (%) | Reaction Pressure (Kg/cm²G) | Reaction Temperature (°C) | Contact Time (sec) |
|---|---|---|---|---|---|---|---|---|---|
| | $C_3H_6$ | $NH_3$ | Air | $O_2$ | $N_2$ | | | | |
| 13 | 1 | 1.20 | 10.5 | 0 | 0 | 7.9 | 0.1 | 440 | 4.0 |
|    | 1 | 1.00 | 10.5 | 0 | 0 | 8.0 | 0.1 | 440 | 4.0 |
|    | 1 | 0.90 | 10.5 | 0 | 0 | 8.1 | 0.1 | 440 | 4.0 |
| 20 | 1 | 1.20 | 10.5 | 0 | 0 | 7.9 | 0.1 | 460 | 6.0 |
|    | 1 | 1.00 | 10.5 | 0 | 0 | 8.0 | 0.1 | 460 | 6.0 |
|    | 1 | 0.20 | 10.5 | 0 | 0 | 8.1 | 0.1 | 460 | 6.0 |
| 12 | 1 | 1.00 | 9.5 | 0 | 0 | 8.7 | 0.1 | 430 | 4.0 |
| 25 | 1 | 1.00 | 9.5 | 0 | 0 | 8.7 | 0.1 | 460 | 5.3 |
| 13 | 1 | 1.05 | 9.6 | 0 | 0 | 8.6 | 0.2 | 440 | 4.5 |
| 20 | 1 | 1.10 | 10.1 | 0 | 0 | 8.2 | 0.2 | 460 | 6.0 |
| 21 | 1 | 1.10 | 10.5 | 0 | 0 | 7.9 | 0.2 | 470 | 7.0 |
| 12 | 1 | 1.15 | 10.5 | 0 | 12.35 | 4.0 | 0.1 | 430 | 4.0 |
|    | 1 | 1.15 | 2.41 | 1.69 | 0 | 16.0 | 0.1 | 430 | 4.5 |
| 20 | 1 | 1.15 | 10.5 | 0 | 12.35 | 4.0 | 0.1 | 450 | 5.0 |
|    | 1 | 1.15 | 2.41 | 1.69 | 0 | 16.0 | 0.1 | 450 | 5.0 |
| 13 | 1 | 1.05 | 11.0 | 0 | 0 | 7.7 | 1.0 | 430 | 4.0 |
| 20 | 1 | 1.05 | 11.0 | 0 | 0 | 7.7 | 1.0 | 450 | 6.0 |

| Catalyst | Results of Reaction $C_3H_6$ Conversion (%) | | | | | | Total $C_3H_6$ Conversion (%) | AN Selectivity (%) | $NH_3$ Balance[1] (%) | Remarks |
|---|---|---|---|---|---|---|---|---|---|---|
| | AN | $CH_3CN$ | HCN | $CO_2$ | CO | AL | AA | | | | |
| 13 | 84.1 | 0.4 | 4.7 | 6.6 | 1.9 | 0.0 | 0.0 | 97.7 | 86.1 | 97.6 | Effect of |
|    | 83.8 | 0.3 | 4.5 | 6.8 | 2.1 | 0.2 | 0.0 | 97.7 | 85.7 | 98.2 | a reduction |
|    | 83.7 | 0.2 | 4.1 | 7.2 | 2.3 | 0.6 | 0.0 | 98.1 | 85.3 | 97.5 | in $NH_3/C_3H_6$ |
| 20 | 77.5 | 0.5 | 6.9 | 9.5 | 3.4 | 0.1 | 0.0 | 98.2 | 78.9 | 99.4 | molar ratio |

Table 3-continued

| | | | | | | | | | | | |
|---|---|---|---|---|---|---|---|---|---|---|---|
| | 76.3 | 0.5 | 6.5 | 10.4 | 3.6 | 1.2 | 0.0 | 98.5 | 77.5 | 98.6 | (See FIG. 10) |
| | 74.2 | 0.2 | 5.8 | 11.1 | 4.3 | 3.1 | 0.0 | 98.7 | 75.2 | 99.1 | |
| 12 | 83.1 | 0.3 | 4.6 | 7.0 | 2.0 | 0.3 | 0.0 | 97.3 | 85.4 | 98.4 | Effect of reduction in air/ |
| 25 | 78.6 | 0.7 | 5.4 | 8.4 | 3.6 | 1.3 | 0.0 | 98.0 | 80.2 | 99.0 | $C_3H_6$ molar ratios |
| 13 | 83.5 | 0.3 | 4.3 | 6.5 | 2.1 | 0.3 | 0.0 | 97.0 | 86.1 | 100.2 | 830 hrs.  Long |
| 20 | 75.9 | 1.2 | 6.8 | 10.3 | 3.9 | 0.0 | 0.0 | 98.1 | 77.4 | 98.8 | 800      hour test |
| 21 | 75.6 | 2.3 | 4.8 | 12.7 | 2.7 | 0.8 | 0.0 | 98.9 | 76.4 | 99.2 | 30       (See FIG. 11) |
| 12 | 89.3 | 0.3 | 4.0 | 6.7 | 1.4 | 0.0 | 0.0 | 97.5 | 87.4 | 100.0 | Effect of the |
| | 80.7 | 0.6 | 5.8 | 8.2 | 2.5 | 0.0 | 0.0 | 97.8 | 82.5 | 98.8 | concentration |
| 20 | 79.2 | 0.8 | 5.9 | 8.1 | 3.2 | 0.1 | 0.0 | 97.3 | 81.4 | 99.2 | of $C_3H_6$ (FIG. |
| | 70.8 | 1.5 | 7.3 | 11.8 | 4.8 | 0.3 | 0.0 | 96.5 | 73.4 | 101.1 | 12) |
| 13 | 80.3 | 0.4 | 5.2 | 8.9 | 2.4 | 0.1 | 0.0 | 97.3 | 82.5 | 97.2 | Effect of reduction in pressure |
| 20 | 70.1 | 1.4 | 7.1 | 12.4 | 5.1 | 0.4 | 0.0 | 96.5 | 72.6 | 98.7 | (See FIG. 13) |

Notes:
AN: acrylonitrile
AL: acrolein
AA: acrylic acid
$^{(1)}NH_3$: balance: the figure is smaller when there is combustion of $NH_3$.

While the invention has been described in detail and with reference to specific embodiments thereof, it will be apparent to one skilled in the art that various changes and modifications can be made therein without departing from the spirit and scope thereof.

What is claimed is:

1. A process for preparing acrylonitrile from propylene, which comprises contacting a mixture of propylene, molecular oxygen and ammonia in the vapor phase at a temperature of about 380° to about 500° C and a pressure of about atmospheric pressure to about 3 Kg/cm² G with a catalyst composition comprising active components of the following empirical formula

$$Fe_aSb_bMe_cTe_dQ_eR_fO_g$$

wherein

Me is at least one element selected from the group consisting of V, Mo and W; Q is at least one element selected from the group consisting of Cu, Mg, Zn, La, Ce, Al, Cr, Mn, Co, Ni, Bi and Sn; and R is at least one element selected from the group consisting of P and B; a, b, c, d, e, f and g each represents atomic ratios, and when a is 10, b is 15 to 60, c is 1 to 10, d is 0.5 to 10, e is 0.1 to 10, f is 0 to 5, and g represents the number of oxygen atoms corresponding to the oxides resulting from the combination of the above active components, wherein the Me and Te components are substantially dissolved in the iron-antimony oxide compound having the formula $FeSbO_4$ to form a solid solution when a slurry containing said components described above, the slurry being obtained by intimately mixing the Me and Te components with the Fe and Sb components along with the Q components and R components, if present, is dried and finally calcined at a temperature of about 500° C to about 900° C.

2. The process of claim 1, wherein said catalyst is calcined for about 1 to about 50 hours at a temperature of about 200° C. to about 600° C., and then for about 1 to about 50 hours at a temperature of about 500° C. to about 900° C.

3. The process of claim 1, wherein the source of said molecular oxygen is air.

4. The process of claim 1, wherein the molar ratio of propylene to oxygen to ammonia in the starting gaseous mixture is about 1:1:0.8 to about 1:4:3.

5. The process of claim 1, wherein the molar ratio of propylene to oxygen to ammonia in the starting gaseous mixture is 1:1.5:0.9 to 1:2.5:1.5.

6. The process of claim 1, wherein said catalyst is supported on a silica carrier.

7. The process of claim 5, wherein said contacting is at a temperature of about 400° C. to about 470° C.

8. The process of claim 5, wherein said contacting is at a pressure of about atmospheric pressure to about 2 Kg/cm² G.

9. The process of claim 1, wherein said Q components and R components are added to a slurry obtained on mixing the Me and Te components and the Fe and Sb components.

10. The process of claim 1, wherein the Q components and R components are added subsequent to the preparation of the slurry of the Me and Te components with the Fe and Sb components but prior to final calcining.

* * * * *

UNITED STATES PATENT AND TRADEMARK OFFICE
CERTIFICATE OF CORRECTION

PATENT NO. : 3,988,359
DATED : October 26, 1976
INVENTOR(S) : Shigeru SAITO et al It is certified that error appears in the above—identified patent and that said Letters Patent are hereby corrected as shown below:

Claim 1, col. 19, line 44, delete "c is 1 to 10" and insert --c is greater than b and less than or equal to 10--.

Signed and Sealed this sixteenth Day of August 1977

[SEAL]

Attest:

RUTH C. MASON
Attesting Officer

C. MARSHALL DANN
Commissioner of Patents and Trademarks